United States Patent
Shimizu et al.

(10) Patent No.: US 10,085,631 B2
(45) Date of Patent: Oct. 2, 2018

(54) METHOD FOR GENERATING EYEGLASS-PRESCRIPTION ASSISTING INFORMATION

(71) Applicant: NIDEK CO., LTD., Gamagori-shi, Aichi-ken (JP)

(72) Inventors: Kazunari Shimizu, Toyokawa (JP); Shirohisa Kobayashi, Nukata (JP)

(73) Assignee: NIDEK CO., LTD., Gamagori (JP)

( * ) Notice: Subject to any disclaimer, the term of this patent is extended or adjusted under 35 U.S.C. 154(b) by 0 days.

(21) Appl. No.: 15/475,854

(22) Filed: Mar. 31, 2017

(65) Prior Publication Data

US 2017/0280990 A1 Oct. 5, 2017

(30) Foreign Application Priority Data

Mar. 31, 2016 (JP) ................................. 2016-073732
Mar. 31, 2016 (JP) ................................. 2016-073733

(51) Int. Cl.
*A61B 3/00* (2006.01)
*A61B 3/10* (2006.01)
*A61B 3/103* (2006.01)

(52) U.S. Cl.
CPC ............ *A61B 3/0025* (2013.01); *A61B 3/103* (2013.01); *A61B 3/1015* (2013.01)

(58) Field of Classification Search
CPC ..... A61B 3/0025; A61B 3/103; A61B 3/1015; A61B 3/14; A61B 3/10
USPC .................................................. 351/200–246
See application file for complete search history.

(56) References Cited

U.S. PATENT DOCUMENTS

| 5,907,388 A | 5/1999 | Fujieda | |
|---|---|---|---|
| 2008/0100800 A1* | 5/2008 | Guillen | A61B 3/1015 351/205 |
| 2015/0221125 A1* | 8/2015 | Shimizu | G06K 9/0061 382/128 |
| 2016/0073868 A1* | 3/2016 | Raymond | A61B 3/0025 351/246 |

FOREIGN PATENT DOCUMENTS

| JP | H10108837 A | 4/1998 |
|---|---|---|
| JP | 2006149871 A | 6/2006 |
| JP | 2006-275971 A | 10/2006 |
| JP | 2015-144730 A | 8/2015 |

* cited by examiner

*Primary Examiner* — Mohammed Hasan
(74) *Attorney, Agent, or Firm* — Oliff PLC

(57) ABSTRACT

A CPU of an eyeglass-prescription assisting apparatus is configured to obtain measurement data on an examinee's eye measured by a wavefront sensor, including first distribution data on a refractive error distribution of an examinee's eye and second distribution data on a refractive power distribution in an eyeglass lens to correct the refractive error of the examinee's eye. The CPU further makes arithmetic processing to obtain third distribution data on a refractive error distribution taking correction with the eyeglass lens into consideration based on the first distribution data and the second distribution data.

19 Claims, 9 Drawing Sheets

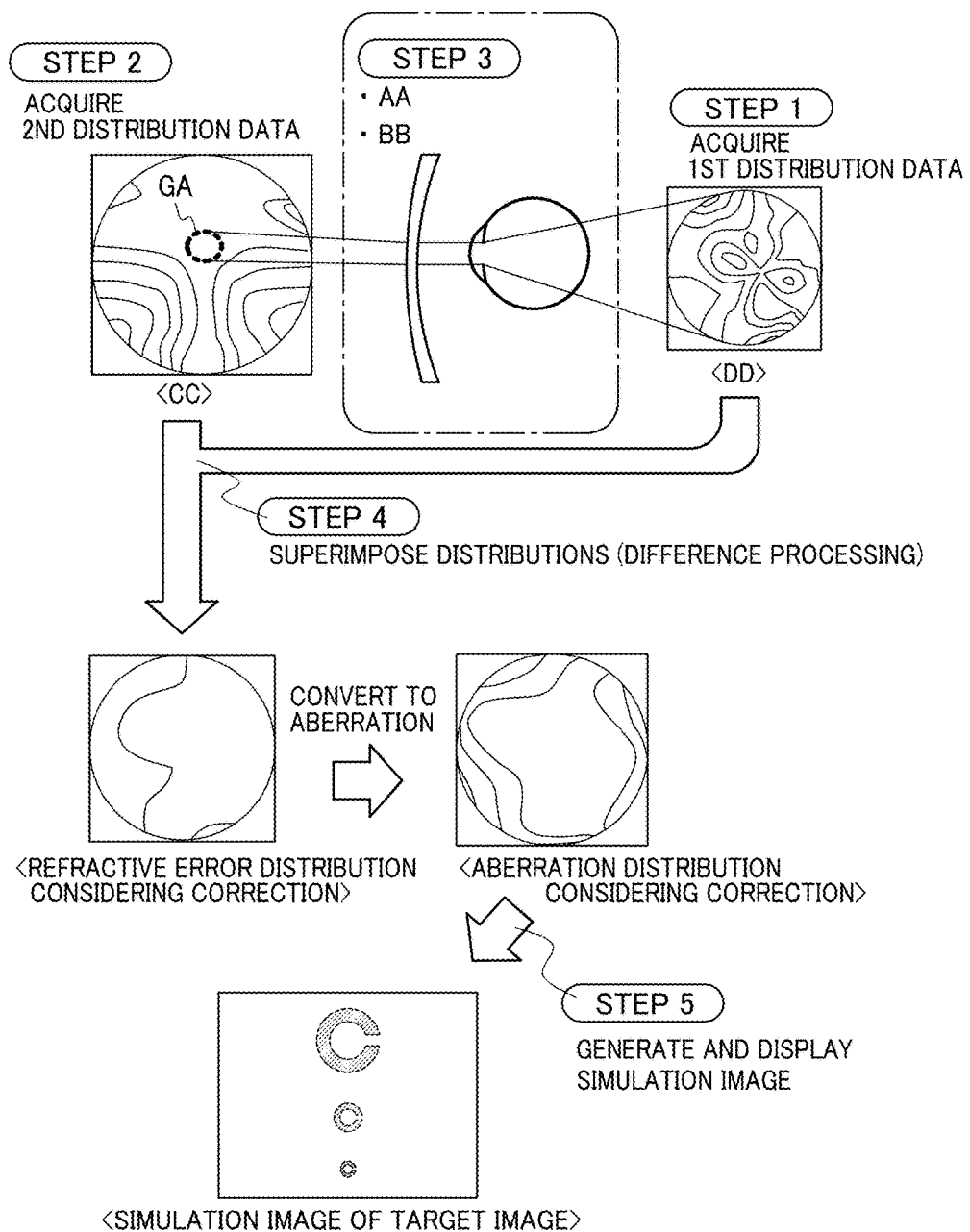

<REFRACTIVE POWER
DISTRIBUTION OF
CORRECTIVE LENS>

GA

<REFRACTIVE POWER ERROR
DISTRIBUTION OF
EXAMINEE'S EYE>

FIG. 7

| TARGET PRESENTING DISTANCE | POSITION OF VISUAL-LINE PASSING REGION ON CORRECTIVE LENS |
|---|---|
| FAR VISION (EX.: 5 m) | FAR-VISION POINT |
| INTERMEDIATE VISION (EX.: 1 m) | PROGRESSIVE ZONE |
| NEAR VISION (EX.: 0.4 m) | NEAR-VISION POINT |

FIG. 8

| TARGET PRESENTING DISTANCE | USAGE PERCENTAGE OF ACCOMMODATION |
|---|---|
| FAR VISION (EX.: 5 m) | 0% |
| INTERMEDIATE VISION (EX.: 1 m) | 30% |
| NEAR VISION (EX.: 0.4 m) | 60% |

METHOD FOR GENERATING EYEGLASS-PRESCRIPTION ASSISTING INFORMATION

CROSS-REFERENCE TO RELATED APPLICATIONS

This application is based upon and claims the benefit of priority from the prior Japanese Patent Applications No. 2016-073732 filed on Mar. 31, 2016 and No. 2016-073733 filed on Mar. 31, 2016, the entire contents of which are incorporated herein by reference.

BACKGROUND

This disclosure relates to a method for generating eyeglass-prescription assisting information to evaluate vision of, or appearance to, an eye of an examinee who wears eyeglasses in order to assist eyeglass prescription.

There has been known an optometry apparatus for measuring a distribution of errors in refractive power of an examinee's eye, a distribution of aberrations, and others. Measurement results using such an apparatus may be utilized to evaluate the appearance to the examinee's eye.

For example, Japanese patent application publication No. 2015-144730 (JP2015-144730A) proposes a method for generating a simulation image showing how a target image appears to an examinee's eye wearing an eyeglass lens for correcting a refractive error of the examinee's eye in consideration of measurement results on the distribution of refractive power errors and additionally the power or diopter of the eyeglass lens.

SUMMARY

However, JP2015-144730A discloses, as a subject matter, simultaneously displaying a simulation image of a target image and information indicating whether or not the simulation image is a simulation obtained when the examinee's eye wears an eyeglass lens in order to allow an examiner and an examinee to easily ascertain simulation conditions. For instance, for an eyeglass lens having different powers by position on the lens, such as a progressive multifocal lens, a method for evaluating the appearance of a target image through such a lens is not sufficiently studied in JP2015-144730A.

The present disclosure has been made to address the above problems and has a purpose to provide a method for generating eyeglass-prescription assisting information allowing more appropriate evaluation of the appearance to an examinee's eye that wears an eyeglass lens.

To achieve the above purpose, one aspect of the present disclosure provides a method for generating eyeglass-prescription assisting information, comprising: an acquisition step of causing a computer to obtain measurement data on an examinee's eye measured by a wavefront sensor, the measurement data including first distribution data on a distribution of refractive error of the examinee's eye and second distribution data on a distribution of refractive power of an eyeglass lens to correct the refractive error of the examinee's eye; and an arithmetic step of causing the computer to obtain third distribution data on a distribution of the refractive error taking correction with the eyeglass lens into consideration based on the first distribution data and the second distribution data.

BRIEF DESCRIPTION OF THE DRAWINGS

FIG. 3 is a diagram showing an operation flow in the eyeglass-prescription assisting apparatus;

FIG. 7 is a table showing positions of a visual-line passing region set according to each target presenting distance in simulation;

FIG. 8 is a table showing what extent accommodation is used to obtain first distribution data selected according to the target presenting distance in simulation;

DETAILED DESCRIPTION OF THE EXEMPLARY EMBODIMENTS

Figure 1:
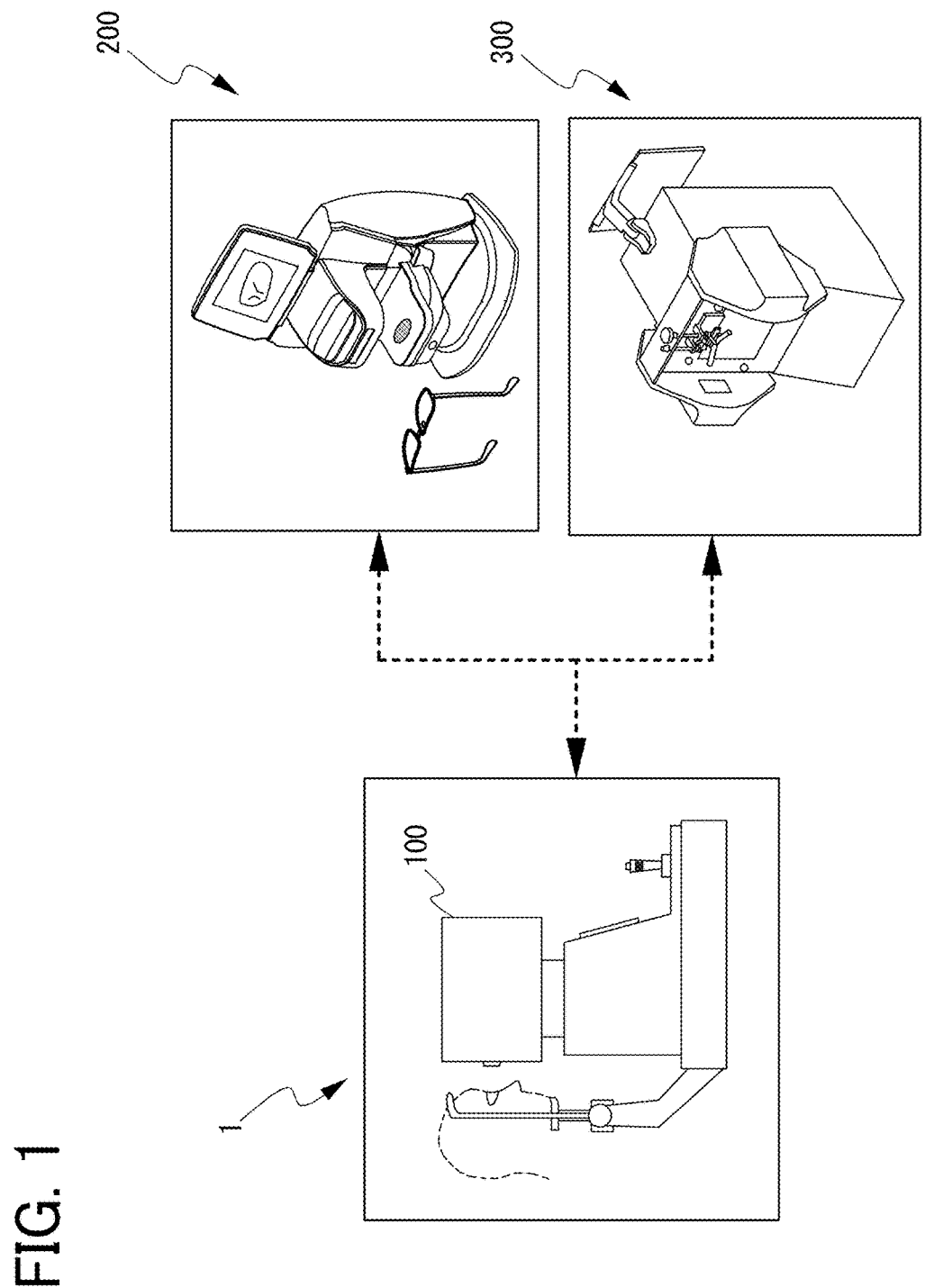
FIG. 1 is a schematic diagram showing a rough overview of an optometry system according to the present disclosure.

An embodiment which is one of typical embodiments of an eyeglass-prescription assisting apparatus and an eyeglass-prescription assisting program embodying this disclosure will be explained below referring to the accompanying drawings. An eyeglass-prescription assisting apparatus 1 and an eyeglass-prescription assisting program are utilized to obtain information for evaluating vision of, or appearance to, an eye to be examined ("examinee's eye") that wears an eyeglass lens. For instance, if the appearance to an examinee who wears his/her own eyeglass lenses (hereinafter, referred to as "previous lens") can be evaluated in eyeglass shops or ophthalmic clinic or hospital (hereinafter, referred to as "eyeglass shop and others"), an examiner becomes able to easily determine whether the examiner should recommend the examinee to replace the eyeglass lens with a new one. Further, for example, if evaluation of the appearance to an examinee when selectively wears various existing eyeglass lenses can be made, easy selection of a new eyeglass lens prescribed for the examinee (hereinafter, referred to as "new lens").

<Outline of System>

The outline of the eyeglass-prescription assisting apparatus (hereinafter, referred to as a "present apparatus") 1 in the embodiment will be first described with reference to FIG. 1. The present apparatus 1 is a computer including a processor that executes the eyeglass-prescription assisting program in the present embodiment.

The present apparatus 1 is configured to acquire data on refractive power distribution of an examinee's eye ("first distribution data" in the present embodiment) and data on refractive power distribution of an eyeglass lens ("second distribution data" in the present embodiment), and process those data. Herein, the data on the distribution of refractive errors of the examinee's eye is obtained as a result of measurement on the examinee's eye using a wavefront sensor. Further, the data on the refractive power distribution of the eyeglass lens may be obtained as a result of measurement of the eyeglass lens using a lens meter. However, the data on the refractive power distribution of the eyeglass lens is not necessarily a measurement result (a measured value), and may also be a design value of the eyeglass lens. The design value is offered by for example a manufacturer of eyeglass lenses (so-called lens manufacturer). The design value may be stored in advance in a data base to which the present apparatus 1 is accessible or a memory 31 (see FIG. 2) contained in the present apparatus 1, or may be input in the present apparatus 1 as occasion arises.

The present apparatus 1 may be an apparatus integral with at least one of the wavefront sensor and the lens meter (in one housing) or may be an apparatus separated from those components (e.g., in separate housings). When the present apparatus 1 is the integral apparatus, the present apparatus 1 may be configured to process a signal from a detector to derive the data on the refractive error of the examinee's eye or the data on the refractive power distribution of the eyeglass lens. When the present apparatus 1 is separated from both the wavefront sensor and the lens meter, the present apparatus 1 may be a general-purpose computer (e.g., a PC, a tablet, etc.) The present apparatus 1 may also be an apparatus that is conceivably used in eyeglass shops and others or may be another apparatus network-linked to client computers placed in eyeglass shops and others on LAN, WAN, or the like. A typical example of the latter apparatus may include a server computer. In this case, the sever computer stores one or more data on the distribution of refractive errors of the examinee's eye E. Successively, the data on the refractive error distribution of the examinee's eye E and the data on the refractive power distribution of the eyeglass lens, which has been stored in advance or is separately transmitted from a client computer, are processed by the eyeglass-prescription assisting program. A processing result is then transmitted to the client computer.

When various types of data, such as data on the refractive error distribution of the examinee's eye and data on the refractive power distribution of the eyeglass lens, are to be transmitted from another apparatus to the present apparatus 1, this signal transmission may be performed online or offline. In the case of offline transmission, any media, for example, a removable disc (e.g., a USB memory), RFID, bar-code, and the like may be utilized for the transmission.

In the present embodiment, the present apparatus 1 is assumed as an apparatus integral with the wavefront sensor.

In the present embodiment, the present apparatus 1 is configured to measure optical characteristics of the examinee's eye E, and measurement data representing a measurement result is stored in a storage section (the memory 31, see FIG. 2) of the present apparatus 1. With the present apparatus 1, at least the refractive error distribution of the examinee's eye E is measured. Thus, the measurement data includes at least the data on the refractive error distribution of the examinee's eye E (hereinafter, referred to as "first distribution data").

The first distribution data is data specifying eye refractive characteristics at each position on a pupil. For instance, the first distribution data may be data expressed in the form of either refractive error or aberration or may be data in any other form than refractive error and aberration. The first distribution data may also be data measured while the examinee's eye E does not exert accommodation or data measured while the eye E exerts accommodation. In each case, further, a plurality of first distribution data may be obtained at different percentages of usage of the accommodation.

As shown in FIG. 1, the present apparatus 1 may be configured to transmit and receive data to or from other apparatuses online or offline. The other apparatuses may be for example any apparatus to be utilized for measurement on eyes or eyeglass lenses or for machining of eyeglass lenses in eyeglass shops and others. FIG. 1 shows, as an example of the other apparatuses, a lens meter 200 and an eyeglass-wearing parameter measuring device 300. However, not limited to the above, the present apparatus 1 may be configured to further transmit and receive data with respect to various devices, such as an autorefractor, a frame tracer, and a lens edger.

The lens meter 200 is configured to obtain measurement data on the refractive power distribution in a wide range (e.g., a full range) of an eyeglass lens. For the detailed structure of the lens meter 200, refer to for example JP2006-275971A and others. The measurement data is stored in the storage section (the memory 31, see FIG. 2) of the present apparatus 1. The measurement data obtained by the lens meter 200 may be transferred to and stored in the storage section (the memory 31, see FIG. 2) of the present apparatus 1. In the present embodiment, from among the measurement data obtained by the lens meter 200, the measurement data on a partial region of an eyeglass lens is acquired as second distribution data by the present apparatus 1.

The second distribution data may be distribution data on power (S: spherical power, C: cylindrical power, A: astigmatic axis angle) at a plurality of points in the partial region of the eyeglass lens. It may also be distribution data on refractive power (Power). The second distribution data includes at least information (refractive power, lens power, aberration, etc.) on the refractive power at three or more extracting points different in distance to a lens center. The second distribution data may be data expressed by aberration as in the first distribution data or may be data expressed in any other form.

The lens meter 200 in the present embodiment is for example configured as below. Specifically, it includes a light projecting optical system for projecting measurement light onto an eyeglass lens and an imaging optical system provided with a two-dimensional light receiving element for imaging a pattern image consisting of a plurality of index images formed by the measurement light passing through the eyeglass lens. As a result of processing the imaged image, the second distribution data is derived. The processing for deriving the second distribution data from the image obtained by the two-dimensional light receiving element may be performed for example by an arithmetic processing unit (e.g., CPU) in a main unit of the lens meter 200 or may be conducted by a CPU 30 (see FIG. 2) of the present apparatus 1. In any case, the second distribution data obtained as a result of the processing is acquired (stored in the memory 31) by the present apparatus 1.

The eyeglass-wearing parameter measuring device 300 (hereinafter, referred to as an "eye position meter") is utilized to obtain measurement data on a relative positional relationship between the eyeglass lens and the examinee's eye E. The measurement data is not limited to for example the position of an eye (an eye point) relative to an eyeglass lens (an eyeglass frame), and may also include a distance between the examinee's eye E and the eyeglass lens (e.g., a vertex distance VD), an orientation of visual line to the eyeglass lens (e.g., determined based on a visual line direction and warp angle of an eyeglass frame), a passing point of a visual line on the eyeglass lens, and others. Furthermore, the measurement data may be obtained for one or more (preferably, two or more) of far vision, near vision, and intermediate vision. In addition, in measuring the distance between the examinee's eye E and the eyeglass lens, the eye position meter 300 measures a distance between at least one point on a lens surface (usually, on a lens back surface) and the examinee's eye E. At that time, the distance between each of a plurality of points on the lens surface and the examinee's eye E may be measured. For instance, a vertex distance VD may be obtained at each of the plurality of different points on the lens surface.

The eye position meter 300 in the present embodiment is configured for example as below. Specifically, this eye position meter 300 includes a camera (an imaging device) for imaging the face of an examinee who is wearing an eyeglass frame, and an arithmetic processing unit (e.g., a CPU) for measuring the relative position of the eye with respect to the eyeglass frame from an imaged image obtained by the camera. The eye position meter 300 shown in FIG. 1 is a separate unit apart from the present apparatus 1, but not limited thereto. For instance, the present apparatus 1 may be integral with the eye position meter 300, that is, they may be housed in a single housing. In the case of an integral structure, the CPU 30 (see FIG. 2) of the present apparatus 1 calculates the measurement data on the eye position. In the present embodiment, the measurement data on the eye position is stored in the storage device (the memory 31, see FIG. 2) of the present apparatus 1.

<Schematic Structure of the Present Apparatus>

Figure 2:
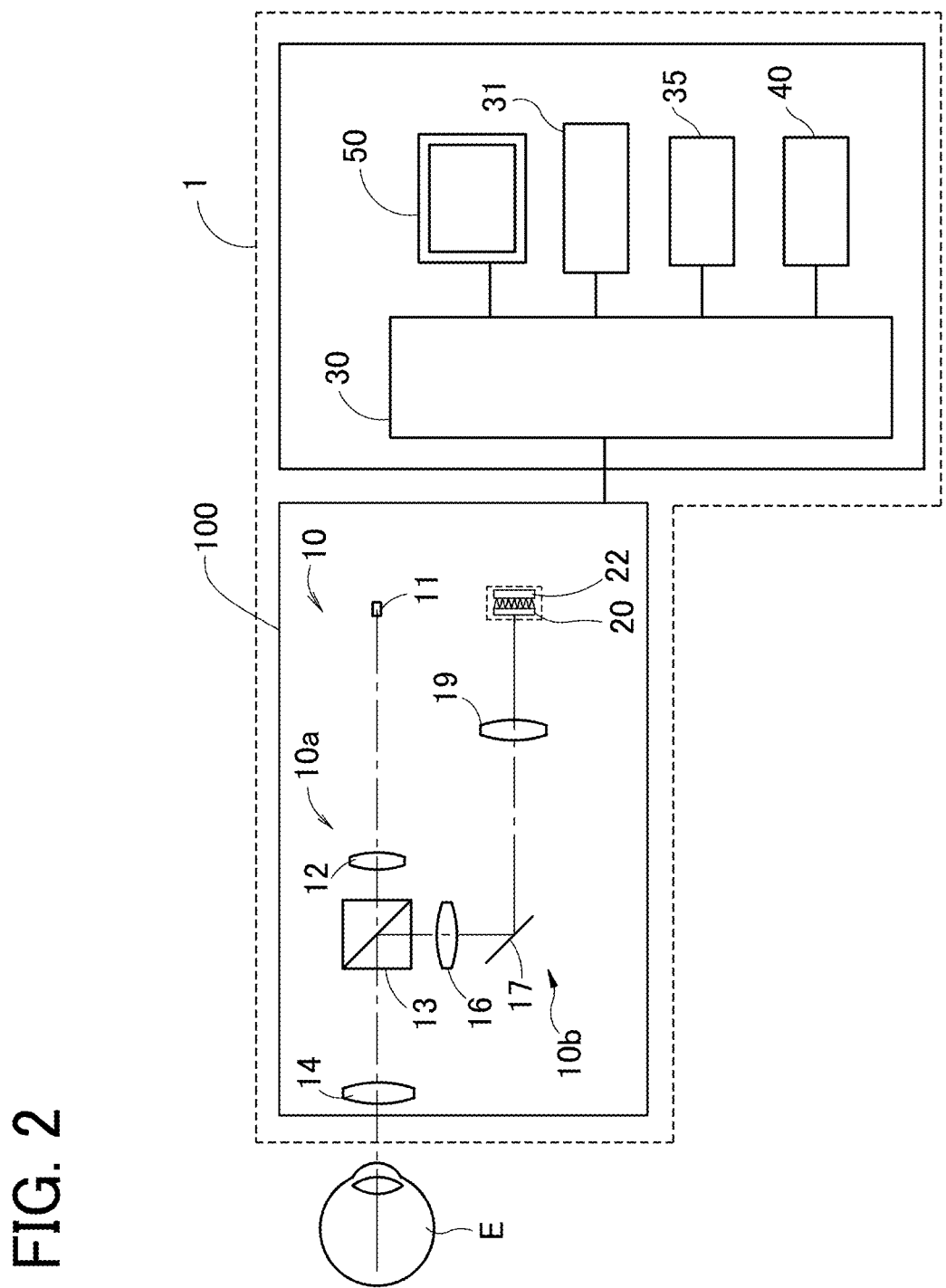
FIG. 2 is a schematic diagram showing a schematic configuration of an eyeglass-prescription assisting apparatus in an embodiment.

The schematic structure of the present apparatus 1 in the present embodiment will be described below with reference to FIG. 2. As shown in FIG. 2, the present apparatus 1 includes at least the CPU (one example of an arithmetic processing unit) 30 and the memory (a storage device) 31. The CPU 30 is a processor for managing main operations to be executed in the present apparatus 1.

The memory 31 is a storage device for storing various types of information and includes at least a volatile storage medium (e.g., a register, a cash, and an RAM) for temporarily storing data and a non-volatile storage medium (e.g., a ROM, a HDD, and a flash memory) for storing a control program, fixed data, and others. In the present apparatus 1, an eyeglass-prescription assisting program may be stored in advance in the non-volatile storage medium. The non-volatile storage medium may include a repeatedly rewritable storage medium. In this case, the repeatedly rewritable storage medium may store in advance the data obtained as a result of execution of the eyeglass-prescription assisting program.

The eyeglass-prescription assisting program in this disclosure does not necessarily need to be stored in the memory 31 of the present apparatus (the computer) 1 and may be configured as below. For instance, the eyeglass-prescription assisting program may be stored in an external storage device 35 attached to the present apparatus 1 so that the eyeglass-prescription assisting program is read from the external storage device 35 by the processor of the present apparatus 1 and executed.

The present apparatus 1 may include, in addition to the CPU 30 and the memory 31, for example the external storage device 35, an operation part 40, a monitor 50, and others. These parts or components are connected to each other through data bus or the like.

The operation part 40 is an input/output interface on which an examiner makes an operation. The monitor 50 displays various types of information on the examinee's eye E in the form of text, graphic, and others. In the present embodiment, display control of the monitor 50 is performed by the CPU 30. In the present embodiment, the CPU 30 also serves as a display control unit.

In the present embodiment, a measurement unit 100 is included in the present apparatus 1. This measurement unit 100 includes a refractive power measuring optical system 10 (also called an eye aberration measuring optical system and hereinafter simply abridged to a "measuring optical system"). The measuring optical system 10 has a detector 22. The measuring optical system 10 is configured to project spot-shaped measurement light into a pupil of an examinee's eye and also detect, through the detector 22, fundus reflection light of the measurement light, extracted from the pupil.

A detection signal to be output from the detector 22 is processed by the CPU 30. As a result, the present apparatus 1 acquires (stores in the memory 31) the measurement data on the examinee's eye from the wavefront sensor, that is, the data on the distribution of refractive error of the examinee's eye (hereinafter, referred to as "first distribution data").

In FIG. 2, the measuring optical system 10 is exemplified by a Shack-Hartmann wavefront sensor, the details of which will be mentioned later, but is not necessarily limited thereto. Specifically, the measuring optical system 10 may be another type of optical system to be utilized for measuring data on the refractive error distribution of the examinee's eye. For example, a Talbot wavefront sensor (for the details, see JP2006-149871A filed by the present applicant) and others may also be utilized. Further, it may be a skiascopic wavefront sensor. Specifically, it is configured to project a slit light to a fundus, detect a reflection light thereof through a light receiving element, and output a phase difference signal at that time. For example, see JPH10-108837(1998)A filed by the present applicant). According to the skiascopic wavefront sensor, the first distribution data on the examinee's eye E can be obtained as a result of processing of the phase difference signal.

Herein, the detailed structure of the measuring optical system 10 shown in FIG. 2 will be described. The measuring optical system 10 includes a light projecting optical system 10a and a light receiving optical system 10b. The light projecting optical system 10a projects spot-shaped light from a measurement light source to a fundus of the examinee's eye E. The light receiving optical system 10b splits the light reflected by the fundus and emerging from the examinee's eye E into more than one light beam, which falls on the two-dimensional light receiving element (one example of the detector).

More concretely, the light projecting optical system 10a includes the light source (the measurement light source) 11, a relay lens 12 and an objective lens 14, which are arranged in this order. The light source 11 is placed in a conjugated position with a fundus. The light receiving optical system 10b includes the objective lens 14, a half mirror 13, a relay lens 16, a total reflection mirror 17, a collimator lens 19, a microlens array 20, and the two-dimensional light receiving element 22, which are arranged in the order from the front of an examinee's eye. The light receiving optical system 10b is configured to establish an optically nearly conjugate relationship between a pupil of an examinee's eye and the microlens array 20. The microlens array 20 is constituted of microlenses arranged two-dimensionally on a plane perpendicular to a measurement optical axis and a light shielding plate to split the fundus reflection light into a plurality of light beams.

Light emitted from the measurement light source 11 is projected to the fundus of the examinee's eye E through the relay lens 12, the objective lens 14, and the pupil of the examinee's eye E. Thus, a point source image is formed on the fundus of the examinee's eye E.

The point source image projected on the fundus of the examinee's eye emerges as reflection light from the examinee's eye E and is collected by the objective lens 14 and then reflected by the half mirror 13. The light reflected by the half mirror 13 is condensed once by the relay lens 16 and then reflected by the total reflection mirror 17. The light reflected by the total reflection mirror 17 passes through the collimator lens 19 and then is split into a plurality of light beams by the lens array 20. These light beams are received by the two-dimensional light receiving element 22. A pattern image received by the two-dimensional light receiving element 22 is stored as image data in the memory 31.

The pattern image formed by the light divided by the lens array 20 into the plurality of light beams and received by the two-dimensional light receiving element 22 changes under the influence of aberration (low order aberration and high order aberration) of the examinee's eye E. Analyzing the pattern image formed by the reflection light from the examinee's eye E as compared with a reference pattern image formed by light with no aberration passing through the lens array 20 enables measurement of a wavefront aberration distribution of the eye and a refractive power distribution. In the present embodiment, such obtained distribution data is stored as the first distribution data in the memory 31.

Moreover, the present apparatus 1 may include an anterior segment camera (not shown) for photographing an anterior segment image including a pupil area of the examinee's eye E. From the anterior segment image, for example, a pupil diameter of the examinee's eye E can be measured. Such an anterior segment camera may be configured to perform imaging by changing over the light quantity of illumination light. For instance, an anterior segment image of the examinee's eye E in each of photopic vision and twilight vision. In this case, it may be configured to selectively adjust the output of the illumination light source to a first illumination light quantity for photographing in photopic vision and a second illumination light quantity for photographing in twilight vision.

As described above, the present apparatus 1 may be connected to the other devices, such as the lens meter 200 and the eye position meter 300. The information output from those other devices are transmitted to the present apparatus 1 and hence stored in the memory 31.

<Description of Operations>

Operations of the present apparatus 1 will be described below referring to FIG. 3 and subsequent figures.

For instance, firstly, the examiner measures optical characteristics of the examinee's eye E on the refractive error distribution by use of the measurement unit 100 of the present apparatus 1. As a result thereof, at least the first distribution data is stored (acquired) in the memory 31 of the present apparatus 1 (Step 1).

The examiner may also measure the optical characteristics of the eyeglass lens by use of the lens meter 200 before or after (alternatively, concurrently with) the measurement of the examinee's eye E. After the measurement, the second distribution data corresponding to the measurement data on the eyeglass lens is input to the present apparatus 1 online or offline. Consequently, the second distribution data is stored (acquired) in the memory 31 of the present apparatus 1 (Step 2).

Further, the pupil diameter of the examinee's eye E may also be measured. In addition, the measurement data on the relative positional relationship between the eyeglass lens and the examinee's eye E (eye point, distance between the eye and the eyeglass lens, orientation of the visual line relative to the eyeglass lens, passing point of the visual line with respect to the eyeglass lens, and others) may be measured by the other devices, such as the eye position meter 300, and stored in the memory 31 of the present apparatus 1 (Step 3). The pupil diameter may be determined as a measured value obtained in either photopic vision or twilight vision. The pupil diameter in photopic vision and the pupil diameter in twilight vision may be measured respectively from an anterior segment image in photopic vision and an anterior segment image in twilight vision, for example.

Based on the first distribution data and the second distribution data, the CPU 30 obtains third distribution data on a refractive error distribution taking correction with an eyeglass lens into consideration (Step 4). For instance, in Step 4, it may be configured to determine a difference of the second distribution data from the first distribution data and obtain the third distribution data as the difference. When the first distribution data and the second distribution data are expressed in different units from each other, Step 4 may include an arithmetic processing to make their units coincident with each other.

In FIG. 3, for instance, the CPU 30 takes a difference between the distribution data on refractive error (one example of the first distribution data) in the examinee's eye E and the distribution data on refractive power (a concrete example of the second distribution data) in the eyeglass lens and consequently generates the third distribution data. When data in the form of aberration is to be obtained as the third distribution data, of course, the refractive power form may be changed to the aberration form. As an alternative, the first distribution data and the second distribution data may be synthesized in the aberration form (i.e., a difference is determined) and hence the third distribution data may be obtained in the aberration form.

The lens meter 200 is configured to obtain, as measurement data, the refractive power distribution in a wide range in the eyeglass lens. However, data on the whole eyeglass lens does not necessarily need to be obtained for evaluation of the appearance to the examinee's eye wearing an eyeglass lens. Therefore, for example, as shown in FIG. 3, it is preferable to primarily consider the data on a partial region GA from among the measurement data on the eyeglass lens. For example, GA may be data on a visual-line passing point of the examinee's eye E in the corrective lens and a vicinity region thereof (collectively referred to as "visual-line passing region" in the present embodiment). Such a position of the region GA may be determined by the CPU 30 based on eye point information obtained by the eye position meter 300.

The size of the region GA may be set according to the pupil diameter of the examinee's eye. The CPU 30 makes superimposition based on the second distribution data in the region GA. The region GA is similar in size to the pupil diameter of the examinee's eye E.

A value of the pupil diameter may be obtained based on for example a photographed image of an anterior segment. The photographed image of the anterior segment may be for example photographed by the present apparatus 1 or by the eye position meter 300, or may be an image photographed by another device. The pupil diameter may be selected from one of a value determined in photopic vision and a value determined in twilight vision. Further, the pupil diameter does not necessarily need to be detected based on the photographed image of the anterior segment. For instance, it may be set based on a pupil diameter the examiner manually enters on the operation part 40 or may be an estimated value according to the age of an examinee, or may be a simple constant value.

Furthermore, to derive the size of the region GA, parameters other than the pupil diameter may also be taken into consideration. For example, a relative positional relationship between an eyeglass lens and the examinee's eye E may also be considered. Concrete examples of the positional relationship include an eye point, a distance between an eye and an eyeglass lens, an orientation of a visual line with respect to an eyeglass lens, a passing point of a visual line with respect to an eyeglass lens, and others. Further, the power of an eyeglass lens may also be taken into account.

The position of the region GA does not necessarily need to be set based on the eye point information. For example, the region GA may be set to a position of a distinctive point of an eyeglass lens, such as a lens center and a near-vision point or a far-vision point in a progressive multifocal lens, but is not limited thereto. The region GA may also be set to any other position on the eyeglass lens. The position of the region GA may also be automatically or manually set on the eyeglass lens.

For automatic setting, for instance, the CPU 30 may be configured to determine the type of a lens (e.g., any one of a spherical lens, a bi-focal lens, and a progressive multifocal lens) based on the second distribution data and set the region GA to a position according to the determined type. For instance, the region GA may be set to at least one of the aforementioned distinctive points of the eyeglass lens.

Figure 4A:
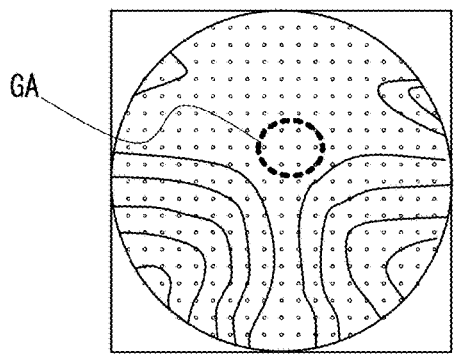
FIGS. 4A and 4B are diagrams showing extracting points of data on refractive power distributions of each of a corrective lens and an examinee's eye.
Figure 4B:
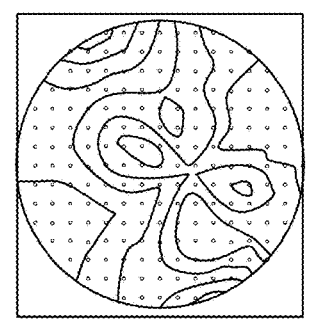

As shown in FIGS. 4A and 4B, it is conceivable that the positions of and the number of extracting points of the first distribution data on the pupil of the examinee's eye E do not correspond to those of extracting points of the second distribution data on the eyeglass lens (concretely, the region GA). Such a situation may occur, for instance, when the number of the extracting points per unit area is different between the measurement unit 100 and the lens meter 200 or when the visual line direction is slanted with respect to the eyeglass lens. The extracting points here may be measuring points of refractive power. When the second distribution data is a design value of an eyeglass lens, each extracting point on that eyeglass lens may also be a typical point on design indicating refractive power. The dots arranged in a reticular pattern in a map (a distribution) shown in FIGS. 4A and 4B represent the extracting points of data in each map.

In contrast, in the present embodiment, the distributions of at least one of the refractive power and the aberration are superimposed after at least one of the number or the positions of the extracting points of the first distribution data on the pupil of the examinee's eye E and the extracting points of the second distribution data on the eyeglass lens (concretely, the region GA) are adjusted to match with each other. This matching method may be selected from various methods.

For example, it may be arranged to derive a function fitting to any one of the refractive power distribution and the aberration distribution on the examinee's eye E or the eyeglass lens from a plurality of extracting point values, and then perform the superimposing based on the derived function. As a result of the matching processing described above, at least either the refractive power distributions or the aberration distributions of the examinee's eye E and the eyeglass lens can be superimposed excellently.

Further, in matching between the first distribution data and the second distribution data, the relative positional relationship between the eyeglass lens and the examinee's eye E may also be taken into consideration. When the visual line direction is slanted with respect to the eyeglass lens, the second distribution data in the region GA may be corrected about a component intersecting with a lens axis of the eyeglass lens in the visual line direction to achieve matching between the first distribution data and the second distribution data.

<Display of Simulation Image>

The CPU 30 creates for example a simulation image based on synthesized distribution data (a result of superimposing) of the first distribution data and the second distribution data (Step 5). In the present embodiment, the simulation image represents an "image simulating a target image formed on a fundus of the examinee's eye E that wears the eyeglass lens" unless otherwise specified. The appearance of the target image to the examinee's eye E wearing an eyeglass lens is represented by the simulation image. This simulation image is displayed for example on the monitor 50.

The target utilized in the simulation image may also include optotypes for a subjective test as shown in FIG. 3 (e.g., an ETDRS optotype, a resolution chart, an astigmatism chart, etc.). Further, other targets, such as a landscape chart and a point image (a point optotype), may also be utilized as the target for the simulation image. A simulation image formed by a point image may be an image created by visualization of an intensity point spread function (PSF) obtained by Fourier transform of the superimposition result of the wavefront aberration. In contrast, the simulation image of optotypes such as a subjective test optotypes may be formed by image processing (e.g., convolution integral) of the optotype and the intensity point spread function (PSF) or may be formed by image processing (convolution integral) of the optotype and an optical transfer function (OTF) obtained by further Fourier transform of the intensity point spread function (PSF).

Figure 5:
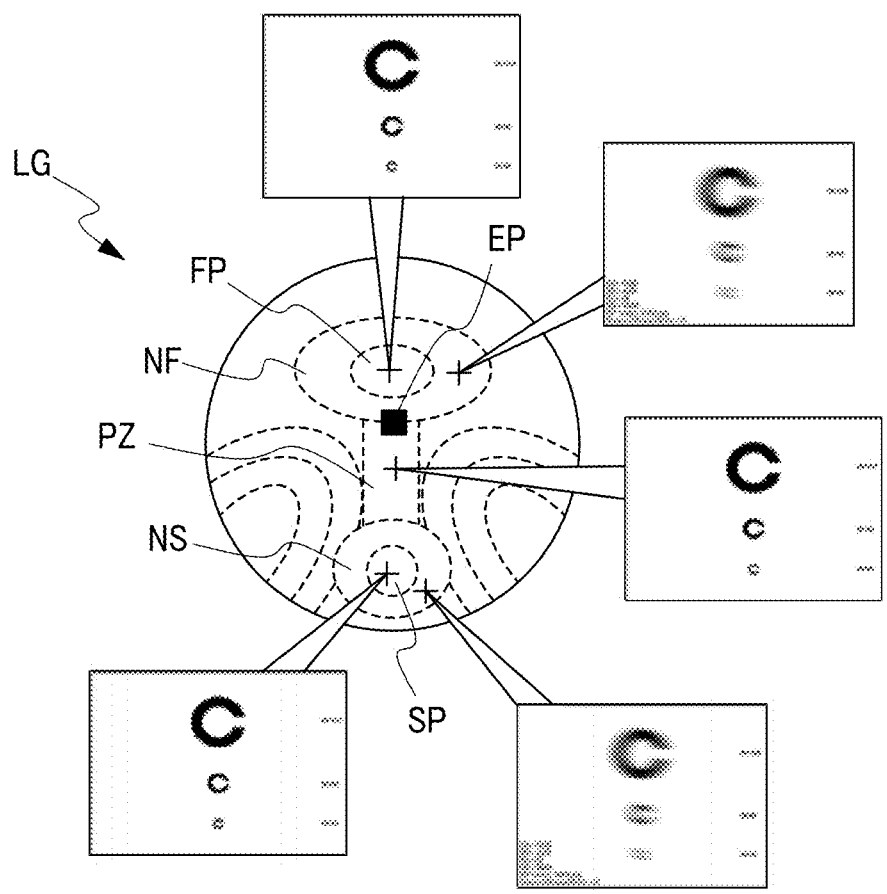
FIG. 5 is a diagram showing a first display example of a simulation image.

The simulation image may be displayed together with the information indicating the position of a region (herein, the region GA) on the eyeglass lens, of which the second distribution data has been utilized to create the simulation image. Such a display of the simulation image allows an examiner to easily ascertain through which region of the lens the appearance is caused. For instance, as shown in FIG. 5, a lens graphic LG representing an eyeglass lens may be displayed together with simulation images and further an indication showing the position of the region GA corresponding to the simulation image (i.e., an indication of positional information) may be provided. In FIG. 5, for example, lead lines from the simulation images in the form of dialogue balloons and cross marks (which are one example of passing point information) indicate the position of the region GA corresponding to each simulation image on the lens graphic LG. However, the display form is not limited to that shown in FIG. 5 and any other display form may be adopted as long as it allows ascertainment of a corresponding relationship between the simulation images and the region GA.

A method for displaying the position of the region GA is not necessarily limited to the method utilizing the lens graphic LG. For example, the CPU 30 may display, together with the simulation image(s), text information representing the position of the region GA in the eyeglass lens (one example of visual-line passing position information). The text information may include text indicating a distinctive point of the eyeglass lens; for example, a lens center, a far-vision point, a near-vision point, a progressive zone, a far-vision point peripheral part, and a near-point peripheral part, or a coordinate having a reference point (e.g., an origin) at the lens center or others, or any other elements.

The lens graphic LG may also include a distinctive region graphic to represent the position of the lens distinctive point. The distinctive region graphic may also be an index placed in the position of the distinctive point in the lens graphic LG. Further, it may be a map on the lens graphic LG to specify the distinctive point. When the eyeglass lens is a multifocal lens, the distinctive point graphic is a graphic to specify at least a far-vision point and a near-vision point. An example of the map is shown in FIG. 5. The lens graphic LG in FIG. 5 is a graphic on the progressive multifocal lens. FIG. 5 illustrates a distinctive point graphic in a form sectionalizing the lens graphic LG into a plurality of regions with contour lines indicating lens powers. As shown in FIG. 5, in the distinctive point graphic in the progressive multifocal lens, at least a far-vision point FP and a near-vision point SP are indicated, but not limited thereto. As another example, each distinctive point, such as a progressive zone PZ, a far-vision point peripheral part NF, a near-vision peripheral part NS, may be shown in the distinctive point graphic.

As shown in FIG. 5, when the position of the region GA is indicated by use of the lens graphic LG, the presence of the distinctive point graphic allows the examiner to more easily ascertain through which region of the eyeglass lens the appearance of the simulation image is obtained.

Further, a plurality of simulation images for different positions of the region GA from each other may be created.

The plurality of simulation images may be displayed in a list on the monitor 50 as shown in FIG. 5. In this case, as shown in FIG. 5, the information representing the position of the region GA corresponding to each simulation image may be displayed on the monitor 50. This makes it is easy for the examiner to multilaterally ascertain the appearance to the examinee's eye E wearing the eyeglass lens.

Further, one or some of the plurality of simulation images may be selectively displayed on the monitor 50. For instance, one of the simulation images for different positions of the visual-line passing region may be switched and displayed with time. At that time, the CPU 30 may switchingly display the simulation image as to present changes in appearance caused when the visual line moves (i.e. the visual line passes through the visual-line passing region) because of turning of the eye.

Figure 6:
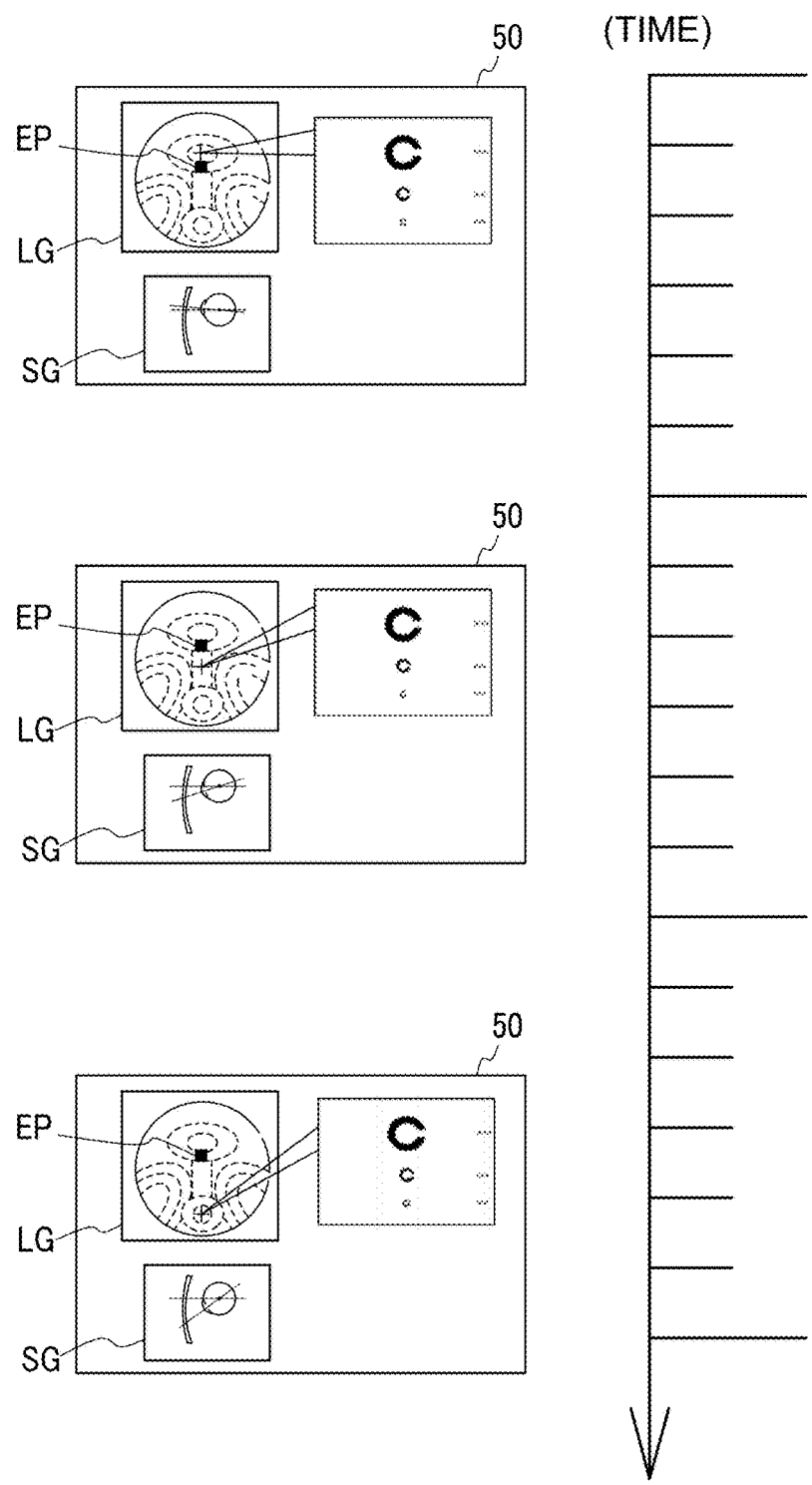
FIG. 6 is a diagram showing a second display example of a simulation image, describing changes in appearance associated with transition of a visual line.

As shown in FIG. 6, for instance, when the eyeglass lens estimated to be worn is a progressive multifocal lens, the simulation images corresponding to transition of the visual line along the progressive zone of the eyeglass lens may be displayed by changeover. In this case, as shown in FIG. 6, switch display may be performed as to indicate changes in target image caused when the visual line moves at least from the far-view point to the near-view point. Such switch display conducted as above enables the examiner to more appropriately ascertain the feeling of wearing the eyeglass lens. For instance, the above switch display allows easy check of the level of uncomfortable feeling to an examinee based on the changes in appearance during movement of the visual line.

Moreover, the information representing the position of the visual-line passing region (passing position information) may be switchingly displayed in conjunction with the simulation images. In FIG. 6, a leading end position of the balloon line from the simulation image and the position of the cross mark are moved in conjunction with the simulation image. Accordingly, the examiner can ascertain real-time the position of the visual-line passing region during switch display of the simulation image.

The transition speed of the visual line to be estimated in the aforementioned switch display of the simulation images may be adjustable. For instance, the transition speed may be set by the CPU 30 based on an operation on the operation part 40. The switch display performed at the set transition speed enables the examiner to ascertain the feeling of wearing the eyeglass lens in various situations.

Even though the details will be described later, a side graphic SG in FIG. 6 indicates a positional relationship of the examinee's eye and a corrective lens seen from side. This side graphic SG is also changed over in conjunction with switch display of the simulation image. This shows a transition situation of the visual-line passing region when the examinee's eye E and the corrective lens are seen from side.

The simulation image simulates the appearance of the target placed at a certain presenting distance from the examinee's eye E. This presenting distance of the target may be selected from a plurality of values. The CPU 30 may be configured to select the presenting distance from any values or from previously determined values. For example, this presenting distance may be selected from three-level values for Far-vision, Near-vision, and Intermediate-vision.

In this case, for example, the CPU 30 may be configured to select a presenting distance of a target and create a simulation image in consideration of the selected presenting distance. Concrete examples are shown as below. The concrete examples may be executed in combination or may be partly performed.

Herein, one concrete example shows that the presenting distance of the target is considered in creating the simulation image. For example, the presenting distance may be considered in setting the region GA with respect to the eyeglass lens. Specifically, when the eyeglass lens is a multifocal lens (e.g., a bi-focal lens, a progressive multifocal lens, etc.), the region GA may be set to a region corresponding to the presenting distance. The simulation image may be generated based on the second distribution data in the set region GA and the first distribution data.

A table in FIG. 7 exemplifies a method for setting the region GA in the progressive multifocal lens when the presenting distance of the target is switched to a value for Far vision, a value for Near vision, and a value for Intermediate vision. Specifically, when the presenting distance of the target is for Far vision, the region GA is set to the far-vision point. When the presenting distance of the target is for Near vision, the region GA is set to the near-vision point. Further, when the presenting distance of the target is for Intermediate vision, the region GA is set to the progressive zone. In each case, a simulation image according to the set region GA is created.

For instance, a plurality of pieces of the first distribution data measured for different presenting positions of the target in measurement using the wavefront sensor may be stored in the memory 31. At that time, the accommodation ability of the examinee's eye E may be simultaneously measured. For each of the target presenting distances for Far vision, for Near vision, and for Intermediate vision, which piece of the first distribution data obtained at what percentage of usage of the accommodation ability is utilized in simulation may be appropriately set. For example, for a shorter presenting distance, the first distribution data obtained with a larger usage percentage of the accommodation ability may be utilized.

A table in FIG. 8 exemplifies a method for selecting the first distribution data when the presenting distance of the target is switched to Far vision, Near vision, or Intermediate vision. For example, the following selection may be made to generate a simulation image. Specifically, for the target presenting distance for Far vision, the first distribution data based on measurement of the examinee's eye E not accommodating is selected. For the target presenting distance for Near vision, the first distribution data based on measurement of the examinee's eye E making accommodation with a predetermined percentage is selected. For the target presenting distance for Intermediate vision, the first distribution data based on measurement of the examinee's eye E making intermediate-level accommodation between the above two cases is selected.

Figure 9:
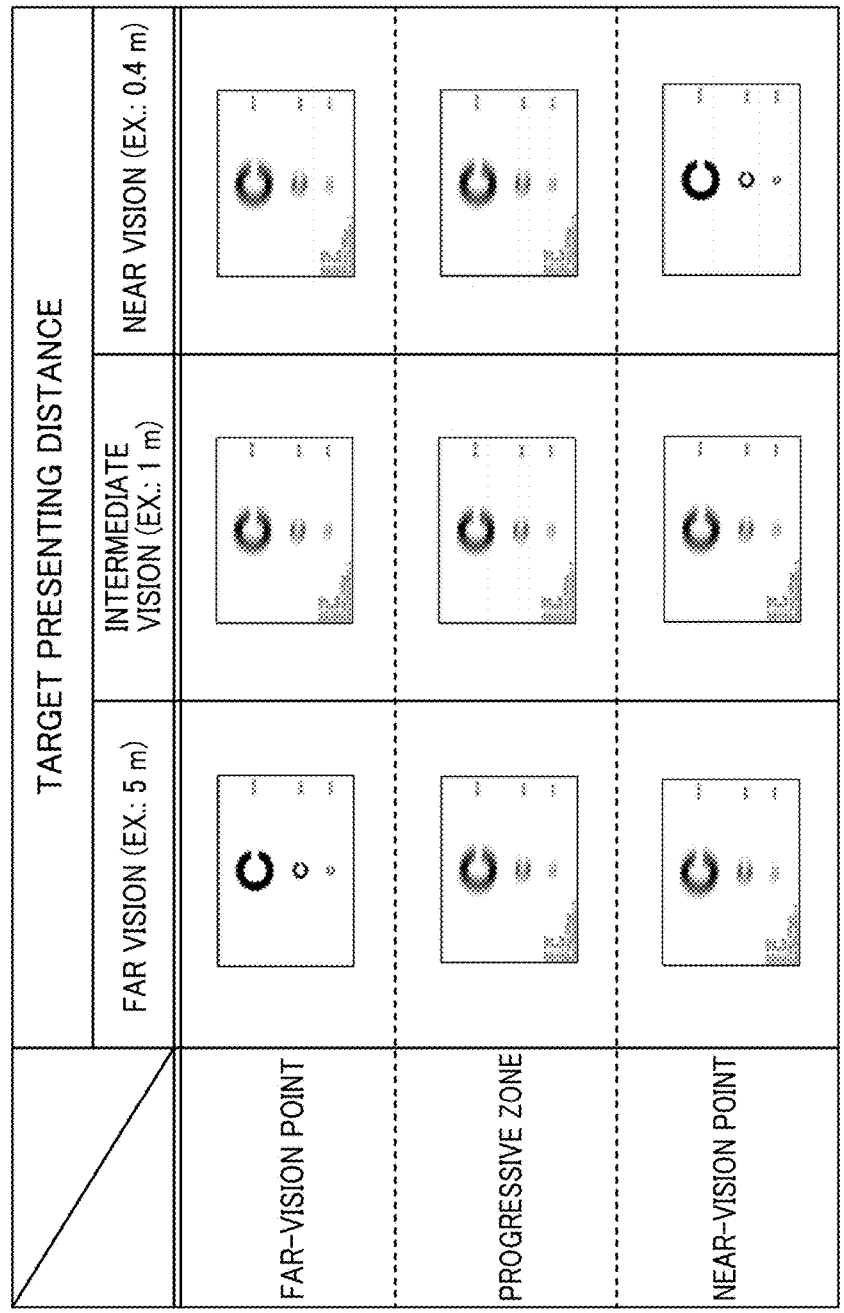
FIG. 9 is a table showing a second display example of simulation images in a list form showing a plurality of simulation images at different target presenting distances.

As shown in FIG. 9, moreover, the CPU 30 may be configured to generate a plurality of simulation images for different target presenting distances from each other, and display those simulation images in a list form on the monitor 50 by associating those images with the presenting distances in each simulation. FIG. 9 shows a display example of the list form of the simulation images generated for different visual-line passing regions and different target presenting distances. Such a display in the list form allows the examiner to easily multilaterally ascertain the appearance to the examinee's eye E wearing the eyeglass lens.

Figure 10:
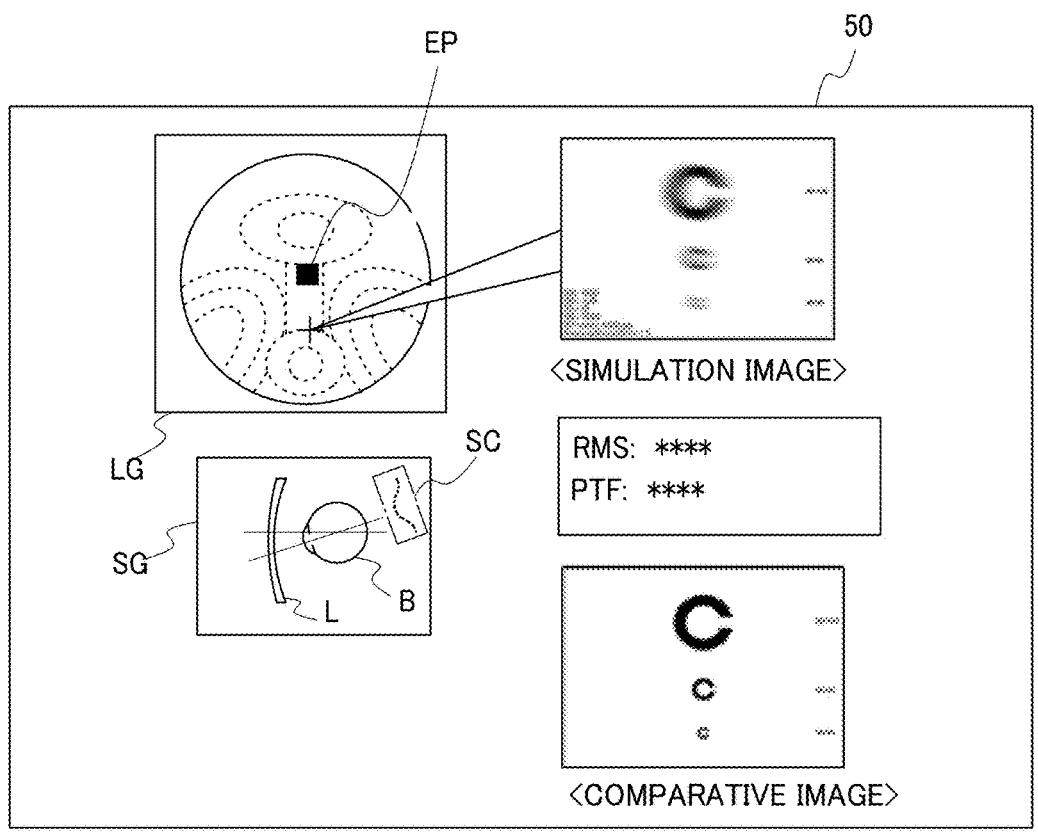
FIG. 10 is a diagram showing a second display example of a simulation image together with graphic to be utilized to change simulation conditions.

Further, the information representing the relative positional relationship between the eyeglass lens and the examinee's eye E may be displayed on the monitor 50 together with the simulation images. For example, in FIGS. 5 and 10, an index EP indicating an eye position appears on the lens graphic LG. The information representing the relative positional relationship between the eyeglass lens and the examinee's eye E may further include a visual-line passing position on a corrective lens, a vertex distance (VD), a visual-line direction with respect to the corrective lens, and others. Those pieces of information may be displayed by graphic, text such as letters and numerical values, or other forms. FIG. 10 shows a concrete example of graphic other than the lens graphic. A side-view graphic SG represents a positional relationship between the examinee's eye E and the corrective lens when seen from side. This graphic is also available for the above information. This graphic shows a visual line, a cumber or warp angle of an eyeglass frame, a vertex distance, a height of an eye with respect to the eyeglass lens, and others.

The simulation image simulates an appearance when the examinee's eye E and the eyeglass lens are disposed in a certain positional relationship. However, the positional relationship between the examinee's eye E and the eyeglass lens in the simulation may also be set to a plurality of positional relationships different from each other. In other words, for example, the positional relationship between the examinee's eye E and the eyeglass lens to be considered in generating the simulation image may be changed according to various commands. Every time the positional relationship is changed, a simulation image based on the changed positional relationship may also be created and displayed.

A command to change the positional relationship between the examinee's eye E and the eyeglass lens in the simulation may be received by the CPU 30 for example in response to an operation input on the operation part 40. Referring to FIG. 10, a concrete example is shown. The following description is given to the concrete example of receiving the above command through a graphic displayed to indicate the positional relationship between the examinee's eye E and the eyeglass lens on the monitor 50. For example, the above command may be received through either the lens graphic LG or the side graphic SG. For instance, with use of a pointing device (one example of the operation part 40), an operation is made to select and move either an index for an eye point or an icon (e.g., the index EP representing an eye position, an eyeball B, and a lens L) on the monitor 50. Accordingly, the position of the index EP and others is changed according to the operation and also the simulation image according to the changed positional relationship may be displayed. Further, the vertex distance, the camber or warp angle of the frame, and others may also be changed by operation to move any index or icon. Thus, a simulation image based on a parameter after the above changing may be created. Initial values of the parameters to be changed as above may be for example a measured value obtained by measurement using the eye position meter 300 and others. Further, even after the parameters are changed, the information representing the initial values may also be displayed on the monitor 50.

The present apparatus 1 configured as above to perform simulation by changing the positional relationship between the examinee's eye E and the eyeglass lens is expected to provide the following advantageous effects, for example. Specifically, when a new lens is to be prescribed for an examinee's eye E, the present apparatus 1 enables the examiner to easily ascertain the placement of the eyeglass lens relative to the examinee's eye E to achieve an appropriate vision based on a simulation image. As a result thereof, the examiner can easily determine an appropriate one from new lens options.

The simulation image may be generated in consideration of Stile-Crawford phenomenon. Specifically, there is known that the sensitivity of photoreceptor cells decreases as an incident angle of light to a fundus is larger (First type Stile-Crawford phenomenon). By considering this phenomenon, the simulation image can be created with an appearance closer to an actual appearance to the examinee's eye E. For instance, an image data on the target image superimposed with an intensity point spread function (PSF) or its Fourier-transformed result to generate a simulation image may be an image data with luminance and contrast that have been made lower in advance in a more peripheral area of the target image. Such an image data may also be stored in advance in the memory 31. Instead, the CPU 30 may execute correction processing on the target image (the simulation image) generated based on the first distribution data and the second distribution data so that the luminance and the contrast is lower as being closer to a peripheral area of the target image. When the simulation image generated in consideration of the Stile-Crawford phenomenon is to be displayed on the monitor 50, a graphic representing the influence of the Stile-Crawford phenomenon may also be displayed together with the simulation image. As one example, in FIG. 10, a graph SC indicating a distribution of sensitivity of an eye in a traversal direction.

Further, the CPU 30 may be configured to calculate an index (concretely, an evaluation parameter) representing the quality of vision of an eye wearing the eyeglass lens based on the first distribution data and the second distribution data. The CPU 30 may display the evaluation parameter together with the simulation image on the monitor 50. Examples of the evaluation parameter include a Strehl ratio, a RMS value of wavefront aberration of an entire examinee's eye, a phase shift (PTF), modulation transfer function (MTF), and others.

The CPU 30 may be configured to extract distribution data on an eyeglass uncorrectable component (uncorrectable distribution data) from the distribution data on wavefront aberration of the examinee's eye (one form of the first distribution data), and generate the simulation image, as a comparative simulation image, based on that uncorrectable distribution data. The simulation image based on the uncorrectable distribution data is an image generated by weighting the simulation image of the target image formed on a fundus of an emmetropic eye by the uncorrectable component data. The comparative simulation image may also be displayed together with the simulation image on the monitor 50. Herein, the uncorrectable distribution data represents a high-order (principally, third or higher order) aberration distribution, corresponding to an aberration component that cannot be corrected by an eyeglass lens. Therefore, the comparative simulation image generated on the uncorrectable distribution data can be utilized as a benchmark of the appearance to the eye wearing the eyeglass lens. The eyeglass uncorrectable component may be indicated by any form other than the comparative simulation image. For example, a value representing the magnitude of the uncorrectable component (e.g., information such as a high-order aberration amount and RMS (root mean square of error of a measured value with respect to an approximate curve of diopter in a circumferential direction), may be displayed on the monitor 50.

The foregoing description is made based on the embodiments; however, the present disclosure is not limited to the aforementioned embodiments and may be embodied in other specific forms.

In the embodiment described above, for instance, a plurality of simulation images for different positions of the region GA from each other on the eyeglass lens are generated and displayed simultaneously or selectively. At that time, if the appearance through the eyeglass lens is different between different points on the eyeglass lens, such a different appearance may be improved by prescription of a custom lens. This custom lens is a lens adjusted with power and a distance between a lens surface and an examinee's eye at each point on the lens.

The CPU 30 may be configured to display a plurality of simulation images for different positions of the region GA on the eyeglass lens and also determine whether or not a comparison result of the appearance of at least two of the simulation images exceeds a reference (a threshold) previously determined. For instance, the appearance may be compared between a region of the eyeglass lens providing a best appearance and other regions. The comparison may be performed by calculating a residual aberration (too large aberration amount to correct by the eyeglass lens) per region and comparing those residual aberrations with each other. When the comparison result exceeds the reference, the CPU 30 may further display the graphic representing the position of a region of the eyeglass lens providing a poor appearance based on the determination result. For instance, a region providing a relatively poor appearance, among the compared regions, may be mapped and displayed on the lens graphic. Thus, an examiner can visually ascertain the position of the region of the eyeglass lens providing poor appearance, the distribution thereof, and others. This result may be utilized by the examiner in recommending a custom lens for an examinee.

At that time, the data on a previous lens utilized in the simulation may be a non-custom lens (e.g., a spherical lens, a bi-focal lens, and a progressive multifocal lens) or may be a custom lens prescribed in the past. In the simulation using the previous lens as a custom lens, aging changes of refractive error of the examinee's eye E, aging changes of eyeglass fitting, and others can be checked from a result of mapping. Therefore, such mapping result may be utilized for not only suggestion of a new lens, but also for client services such as eyeglass maintenance.

For instance, the aforementioned embodiment shows an example of utilizing, as the power information of the corrective lens to be utilized in generating the simulation image, the information on a refractive power distribution at the visual-line passing points (that is, the second distribution data in the region GA). However, the power information of the corrective lens at the visual-line passing points is not necessary to be distribution information having data obtained at a plurality of extracting points. For instance, power information uniquely determined with respect to the visual-line passing points may be utilized. For example, the present modified example may be applied when the measurement data of the lens meter 200 or the design value data on the eyeglass lens is data that powers are assigned one to a region or each of sectionalized regions of the eyeglass lens.

The aforementioned embodiment shows an example of generating a simulation image as the correction result information indicating the appearance to the examinee's eye E based on the third distribution data and representing the result of correction with the eyeglass lens. However, the present disclosure is not necessarily limited thereto. For instance, the correction result information may be a map image representing the third distribution data in the form of a map created by the CPU 30 (e.g., the map shown in FIG. 3). Further, the correction result information may be any other forms, such as graphic, text, and numerical values.

Furthermore, for example, the present disclosure includes the means of solving the following problems (second technical problems) in a conventional art disclosed in for example JP2015-144730A.

<Second Technical Problems>

When the eyeglass lens is a multifocal lens and others, the appearance of the target image may change depending on a position in the eyeglass lens through which a visual line passes, a three-dimensional positional relationship, and other reasons. However, JP2015-144730A does not necessarily provide sufficient study of those viewpoints.

To address such technical problems, the present disclosure can provide the following configurations (first to twentieth methods for generating eyeglass-prescription assisting information) to more effectively display a simulation image representing the appearance to an examinee's eye that wears an eyeglass lens.

<First Method for Generating Eyeglass-Prescription Assisting Information>

A method for generating eyeglass-prescription assisting information includes an acquisition step of causing a computer to obtain a simulation image simulating a target image to be formed on a fundus of an examinee's eye wearing an eyeglass lens, the simulation image being generated based on measurement data on the examinee's eye obtained by a wavefront sensor, corresponding to first distribution data related to a distribution of refractive error of the examinee's eye, and power information of a part of the eyeglass lens to correct the refractive error of the examinee's eye; and a display control step of causing the computer to display positional information representing a position of the part in the eyeglass lens corresponding to the simulation image together with the simulation image on a monitor.

<Second Method for Generating Eyeglass-Prescription Assisting Information>

In the first method for generating eyeglass-prescription assisting information, the display control step includes causing the computer to display a lens graphic simulating the eyeglass lens on the monitor and further superimpose an index representing the position of the part as the positional information onto the lens graphic.

<Third Method for Generating Eyeglass-Prescription Assisting Information>

In the display control step in the second method for generating eyeglass-prescription assisting information, the lens graphic to be displayed by the computer includes a distinctive site graphic to indicate a distinctive site in the eyeglass lens.

<Fourth Method for Generating Eyeglass-Prescription Assisting Information>

In the third method for generating eyeglass-prescription assisting information, the distinctive site graphic is a graphic to specify any one of a far-vision point, a near-vision point, and a progressive zone when the eyeglass lens is a progressive multifocal lens.

<Fifth Method for Generating Eyeglass-Prescription Assisting Information>

In the third method for generating eyeglass-prescription assisting information, the distinctive site graphic is a map representing regions sectionalized per power on the eyeglass lens.

<Sixth Method for Generating Eyeglass-Prescription Assisting Information>

In the first method for generating eyeglass-prescription assisting information, the acquisition step includes causing the computer to obtain at least the simulation image generated based on power information at an eye point corresponding to the position of the examinee's eye with respect to the eyeglass lens when the eyeglass lens is worn on the examinee's eye. The display control step includes causing the computer to display information representing the eye point as the positional information on the monitor.

<Seventh Method for Generating Eyeglass-Prescription Assisting Information>

In the first method for generating eyeglass-prescription assisting information, the acquisition step includes causing the computer to obtain a plurality of the simulation images corresponding to positions of a plurality of the parts different from each other in the single eyeglass lens. The display control step includes causing the computer to display, on the monitor, the plurality of the simulation images for different positions of the part from each other in association with positional information on each simulation image.

<Eighth Method for Generating Eyeglass-Prescription Assisting Information>

In the seventh method for generating eyeglass-prescription assisting information, the display control step includes causing the computer to switchingly display, with time, one of the simulation images for different positions of the part from each other.

<Ninth Method for Generating Eyeglass-Prescription Assisting Information>

In the eighth method for generating eyeglass-prescription assisting information, the display control step includes switchingly displaying the simulation image as to show transition of the position of the part on the eyeglass lens due to turning of the eye.

<Tenth Method for Generating Eyeglass-Prescription Assisting Information>

In the ninth method for generating eyeglass-prescription assisting information, the acquisition step includes obtaining the plurality of the simulation images corresponding to the positions of the plurality of the parts along a progressive zone of the eyeglass lens that is a progressive multifocal lens. The display control step includes switchingly displaying the simulation images as to show transition of the position of the part on the progressive zone.

<Eleventh Method for Generating Eyeglass-Prescription Assisting Information>

In the first method for generating eyeglass-prescription assisting information, there is further included a presenting distance selection step of causing the computer to select a first presenting distance corresponding to a presenting distance of a target for the target image. The acquisition step includes causing the computer to obtain the simulation image generated in consideration of the first presenting distance selected in the presenting distance selection step.

<Twelfth Method for Generating Eyeglass-Prescription Assisting Information>

In the eleventh method for generating eyeglass-prescription assisting information, when the simulation image for the eyeglass lens that is a multifocal lens is to be obtained, the acquisition step includes causing the computer to set the position of the part according to the first presenting distance and further obtain the simulation image based the power information of the part at the set position of the part.

<Thirteenth Method for Generating Eyeglass-Prescription Assisting Information>

In the eleventh method for generating eyeglass-prescription assisting information, the acquisition step includes causing the computer to select any one of a plurality of first distribution data according to a first presenting distance selected in the presenting distance selection step, the first distribution data having been measured with different second presenting distances corresponding to a presenting distance of a fixation target in the wavefront sensor, and further obtaining the simulation image based on the selected first distribution data and the first presenting distance.

<Fourteenth Method for Generating Eyeglass-Prescription Assisting Information>

In the eleventh method for generating eyeglass-prescription assisting information, the acquisition step includes causing the computer to obtain a plurality of the simulation images in the first presenting distances different from each other. The display control step includes causing the computer to display the plurality of the simulation images in a list form in association with the first presenting distances on the monitor.

<Fifteenth Method for Generating Eyeglass-Prescription Assisting Information>

In the first method for generating eyeglass-prescription assisting information, there is further included a second acquisition step of causing the computer to obtain positional relationship information corresponding to information representing a positional relationship between the eyeglass lens and the examinee's eye. The acquisition step includes causing the computer to obtain the simulation image in consideration of a positional relationship between the eyeglass lens and the examinee's eye indicated by the positional relationship information.

<Sixteenth Method for Generating Eyeglass-Prescription Assisting Information>

In the fifteenth method for generating eyeglass-prescription assisting information, there is further included a command receiving step of causing the computer to receive a command to change the positional relationship between the eyeglass lens and the examinee's eye to be considered in the simulation image. The simulation image acquisition step includes causing the computer to obtain the simulation image generated in consideration of the positional relationship changed by the command.

<Seventeenth Method for Generating Eyeglass-Prescription Assisting Information>

A method for generating eyeglass-prescription assisting information includes a third acquisition step of causing a computer to obtain first distribution data on a distribution of refractive error of an examinee's eye corresponding to measurement data on the examinee's eye measured by a wavefront sensor, a partial power information corresponding to power information of a part of an eyeglass lens to correct the refractive error of the examinee's eye, and positional relationship information on a positional relationship between the eyeglass lens and the examinee's eye, and a fourth acquisition step of causing the computer to obtain a simulation image of a target image to be formed on a fundus of the examinee's eye, corresponding to a simulation image for the examinee's eye wearing the eyeglass lens, based on the first distribution data, the partial power information, and the positional relationship information.

<Eighteenth Method for Generating Eyeglass-Prescription Assisting Information>

In the seventeenth method for generating eyeglass-prescription assisting information, there is further included a command receiving step of causing the computer to receive a command to change the positional relationship between the eyeglass lens and the examinee's eye to be considered for the simulation image. The fourth acquisition step includes causing the computer to obtain the simulation image generated in consideration of the positional relationship changed by the command.

<Nineteenth Method for Generating Eyeglass-Prescription Assisting Information>

In the seventeenth method for generating eyeglass-prescription assisting information, there is further included a display control step of causing the computer to display positional information representing the position of the part in the eyeglass lens corresponding to the simulation image together with the simulation image on the monitor.

<Twentieth Method for Generating Eyeglass-Prescription Assisting Information>

In the nineteenth method for generating eyeglass-prescription assisting information, the fourth acquisition step includes causing the computer to further obtain a comparative simulation image generated by weighting a simulation image of a target image formed on a fundus of an emmetropic eye by uncorrectable distribution data corresponding to distribution data of an uncorrectable component in the first distribution data. The display control step includes causing the computer to display the comparative simulation image together with the simulation image on the monitor.

The present disclosure is not limited to the aforementioned embodiments and may be variously changed or modified without departing from the essential characteristics thereof.

What is claimed is:

1. A method for generating eyeglass-prescription assisting information, the method comprising:
   an acquisition step including causing a computer to obtain: (i) measurement data on an examinee's eye measured by a wavefront sensor, the measurement data including first distribution data on a distribution of a refractive error of the examinee's eye, and (ii) second distribution data on a distribution of refractive power of an eyeglass lens to correct the refractive error of the examinee's eye;
   an arithmetic step including causing the computer to generate third distribution data on a distribution of the refractive error of the examinee's eye that is corrected by the eyeglass lens into consideration based on the first distribution data and the second distribution data; and
   a correction result information generating step including causing the computer to generate correction result information based on the third distribution data, the correction result information (i) indicating an appearance of the examinee's eye, (ii) corresponding to a plurality of different points distributed on the eyeglass lens, and (iii) representing a result of correction by the eyeglass lens.

2. The method for generating eyeglass-prescription assisting information according to claim 1, wherein the acquisition step includes causing the computer to obtain measurement data on a partial region as the second distribution data from among the measurement data on the distribution of refractive power of the eyeglass lens measured by a lens meter.

3. The method for generating eyeglass-prescription assisting information according to claim 2, wherein the generation of third distribution data includes causing the computer to match an extracting point of the first distribution data in a pupil of the examinee's eye and an extracting point of the second distribution data in the partial region of the eyeglass lens for at least one of a number of the extracting points or positions of the extracting points.

4. The method for generating eyeglass-prescription assisting information according to claim 2, wherein the arithmetic step includes causing the computer to set a size of the partial region according to a pupil diameter of the examinee's eye.

5. The method for generating eyeglass-prescription assisting information according to claim 2, wherein the arithmetic step includes causing the computer to set the partial region based on a relative positional relationship between the eyeglass lens and the examinee's eye.

6. The method for generating eyeglass-prescription assisting information according to claim 2, wherein the acquisition step includes causing the computer to obtain the second distribution data based on an eye point corresponding to a position of the examinee's eye with respect to the eyeglass lens when the eyeglass lens is worn on the examinee's eye.

7. The method for generating eyeglass-prescription assisting information according to claim 1, wherein the correction result information generating step includes causing the computer to generate a map image of the third distribution data as the correction result information.

8. The method for generating eyeglass-prescription assisting information according to claim 1, wherein the correction result information generating step includes causing the computer to generate a simulation image as the correction result information based on the third distribution data, the simulation image being an image simulating a target image to be formed on a fundus of the examinee's eye wearing the eyeglass lens.

9. The method for generating eyeglass-prescription assisting information according to claim 8, wherein the correction result information generating step includes causing the computer to generate the simulation image based on a Stiles-Crawford phenomenon which is based on a change in a sensitivity of photoreceptor cells in the examinee's eye wearing the eyeglass lens with respect to a change in an incident angle of light to a fundus of the examinee's eye wearing the eyeglass lens.

10. The method for generating eyeglass-prescription assisting information according to claim 8, further comprising a display control step including causing the computer to display, on a monitor, positional information representing a position of a part in the eyeglass lens corresponding to the simulation image together with the simulation image.

11. The method for generating eyeglass-prescription assisting information according to claim 10, wherein the display control step includes causing the computer to display a lens graphic simulating the eyeglass lens on the monitor and superimpose an index representing the position of the part in the eyeglass lens as the positional information onto the lens graphic.

12. The method for generating eyeglass-prescription assisting information according to claim 11, wherein the lens graphic to be displayed by the computer includes a distinctive site graphic to indicate a distinctive site on the eyeglass lens.

13. The method for generating eyeglass-prescription assisting information according to claim 10, wherein the display control step includes switching the display of the simulation image to display a transition of the position of the part on the eyeglass lens due to a turning of the examinee's eye.

14. The method for generating eyeglass-prescription assisting information according to claim 10, further comprising:
a presenting distance selection step including causing the computer to select a first presenting distance corresponding to a presenting distance of a target for the target image,
wherein the acquisition step includes causing the computer to obtain the simulation image generated based on the first presenting distance selected in the presenting distance selection step.

15. The method for generating eyeglass-prescription assisting information according to claim 14, wherein the eyeglass lens is a multifocal lens, and when the simulation image for the eyeglass lens is obtained, the acquisition step includes, causing the computer to:
set the position of the part on the eyeglass lens according to the first presenting distance, and
obtain the simulation image based the refractive power of the part on the eyeglass lens at the set position of the part on the eyeglass lens.

16. The method for generating eyeglass-prescription assisting information according to claim 14, wherein the acquisition step includes causing the computer to:
select any one of the first distribution data according to the first presenting distance selected in the presenting distance selection step, each of the first distribution data being measured with different second presenting distances corresponding to a presenting distance of a fixation target in the wavefront sensor, and
obtain the simulation image based on the selected one of the first distribution data and the first presenting distance.

17. The method for generating eyeglass-prescription assisting information according to claim 14, wherein:
the acquisition step includes causing the computer to obtain a plurality of the simulation images, each at different first presenting distances; and
the display control step includes causing the computer to display the plurality of the simulation images in list form in association with the first presenting distances on the monitor.

18. The method for generating eyeglass-prescription assisting information according to claim 10, further comprising:
a second acquisition step of causing the computer to obtain positional relationship information corresponding to information representing a positional relationship between the eyeglass lens and the examinee's eye,
wherein the acquisition step includes causing the computer to obtain the simulation image based on the positional relationship between the eyeglass lens and the examinee's eye indicated by the positional relationship information.

19. The method for generating eyeglass-prescription assisting information according to claim 18, further comprising:
a command receiving step including causing the computer to receive a command to change the positional relationship between the eyeglass lens and the examinee's eye to be considered in the simulation image,
wherein the acquisition step includes causing the computer to obtain the simulation image generated in consideration of the positional relationship changed by the command.

\* \* \* \* \*